United States Patent [19]

Hagen et al.

[11] Patent Number: 5,519,321
[45] Date of Patent: May 21, 1996

[54] CIRCULARLY POLARIZING LOCAL ANTENNA ARRANGEMENT WITH A MOVABLE ANTENNA

[75] Inventors: Juergen Hagen; Yutaka Watanabe, both of Erlangen, Germany

[73] Assignee: Siemens Aktiengesellschaft, Munich, Germany

[21] Appl. No.: 252,220

[22] Filed: Jun. 1, 1994

[30] Foreign Application Priority Data

Jun. 1, 1993 [DE] Germany .......................... 43 18 134.1

[51] Int. Cl.$^6$ .............................. G01V 3/00; A61B 5/055
[52] U.S. Cl. .................. 324/318; 324/322; 128/653.5
[58] Field of Search .................................. 324/318–322; 128/653, 653.1–653.5

[56] References Cited

U.S. PATENT DOCUMENTS

| | | | |
|---|---|---|---|
| 4,733,190 | 3/1988 | Dembinski . | |
| 4,784,146 | 11/1988 | Mancuso et al. | 324/318 X |
| 4,791,372 | 12/1988 | Kirk et al. | 324/318 |
| 4,891,596 | 1/1990 | Mitomi . | |
| 5,007,425 | 4/1991 | Vanek et al. . | |
| 5,063,933 | 11/1991 | Takahashi | 128/653.5 |
| 5,136,244 | 8/1992 | Jones et al. . | |
| 5,144,241 | 9/1992 | Oppelt et al. . | |
| 5,150,710 | 10/1992 | Hall et al. | 324/318 X |
| 5,166,618 | 11/1992 | Jones et al. . | |
| 5,185,577 | 2/1993 | Minemura . | |
| 5,241,272 | 8/1993 | Friedrich . | |
| 5,280,249 | 1/1994 | Kess . | |
| 5,293,519 | 3/1994 | Yoshino et al. . | |

FOREIGN PATENT DOCUMENTS

| | | |
|---|---|---|
| 0133364 | 2/1985 | European Pat. Off. . |
| 0384061 | 8/1990 | European Pat. Off. . |
| 3918743 | 12/1990 | Germany . |

*Primary Examiner*—Sandra L. O'Shea
*Assistant Examiner*—Mack Haynes
*Attorney, Agent, or Firm*—Hill, Steadman & Simpson

[57] ABSTRACT

A circularly polarizing local antenna for use in a magnetic resonance apparatus is formed by first and second antennae, which are in turn respectively formed by first and second coils. The second coil has an opening surrounding an examination region, through which an examination subject can be introduced. The arrangement includes a coil holder, to which the first coil is attached so as to be movable between first and second positions and to which the second coil is rigidly attached. When the first coil is oriented in the first position, it also surrounds the examination region, with the respective coil axes of the first and second coils being disposed substantially perpendicular to each other. In the first position, the first coil obstructs the opening of the second coil. By moving the first coil from the first position to the second position, the first coil becomes oriented so as to leave the opening of the second coil unobstructed, permitting unimpeded introduction of the examination subject into the examination region.

14 Claims, 8 Drawing Sheets

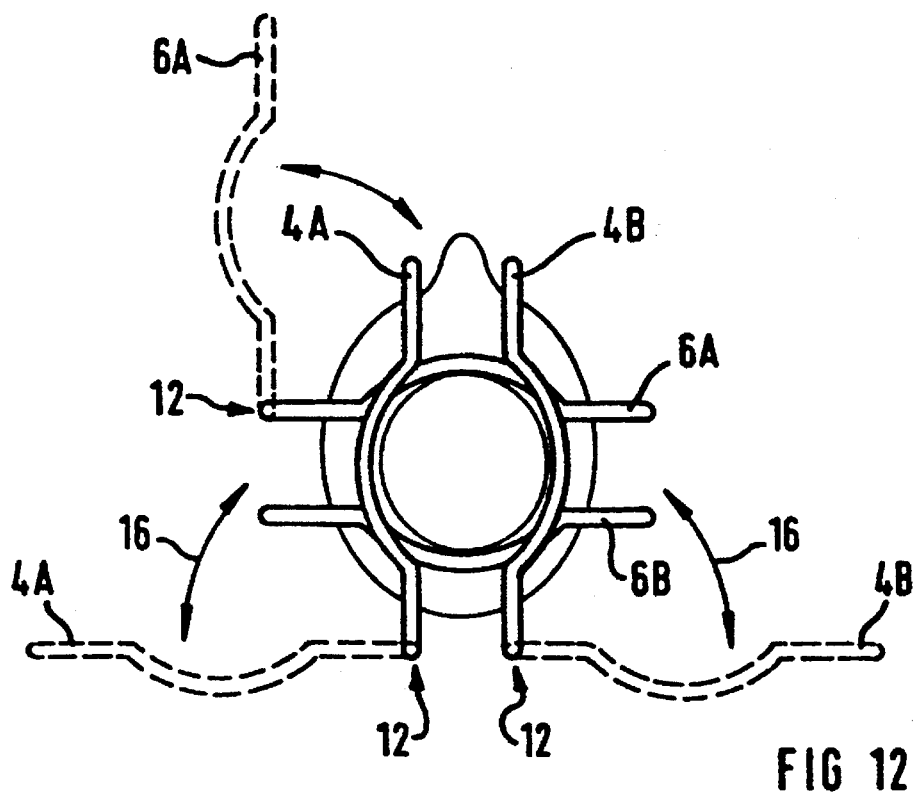
FIG 12
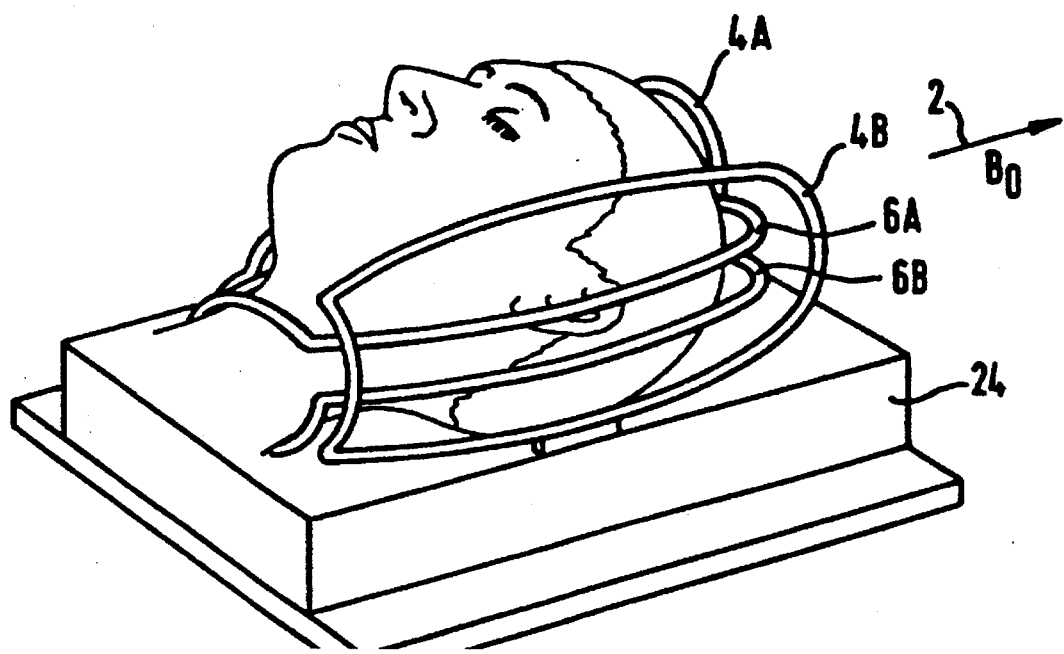

5,519,321

CIRCULARLY POLARIZING LOCAL ANTENNA ARRANGEMENT WITH A MOVABLE ANTENNA

BACKGROUND OF THE INVENTION

1. Field of the Invention

The present invention is directed to a circularly polarizing antenna arrangement for a magnetic resonance apparatus, of the type formed by first and second antennae each in the form of a coil, the coils having respective coil axes disposed substantially perpendicularly relative to each other.

2. Description of the Prior Art

A circularly polarizing antenna arrangement of the type generally described above is disclosed in U.S. Pat. No. 5,144,241. This known antenna arrangement is formed by two coils, each having windings, with the respective coil axes of the coils being disposed perpendicularly relative to each other. The coils are disposed obliquely relative to a patient support, and thus are also disposed obliquely relative to the examination region, so that both coils surround the examination region. The coil area or surface surrounded by each winding is thus substantially larger than the actual cross section of the examination region. The filling factor is therefore low in this known arrangement, which has a disadvantageous influence on the signal-to-noise ratio.

SUMMARY OF THE INVENTION

It is an object of the present invention to provide a circularly polarizing local antenna arrangement of the type formed by first and second antennae which can be oriented so as to surround an examination region with their respective coil axes being disposed substantially perpendicularly relative to each other, the arrangement having a good signal-to-noise ratio.

The above object is achieved in accordance with the principles of the present invention in a circularly polarizing local antenna arrangement wherein the first coil is movably mounted with respect to the second coil so that the first coil can be moved from a position for conducting an examination, wherein the first coil obstructs the opening of the coil, to a second position wherein the first coil leaves the opening of the second coil unobstructed, thereby permitting unimpeded introduction of the examination subject into the examination region.

Due to the movable arrangement of the first coil, the cross section of both coils can be adapted to the cross section of a specific examination region, this examination region in turn being adapted to a particular anatomical shape. The filling factor of the local antenna arrangement thus is high, as a result of which the signal-to-noise ratio also assumes high values.

In an embodiment of the arrangement, the first coil is laterally connected to the coil holder by pivotable joint. The movement of the first coil which leaves the opening of the second coil unobstructed can thus ensue by pivoting the first coil relative to the coil holder and relative to the second coil.

The pivotable joint may also include electrical contacts for supplying or tapping an antenna signal.

In a further embodiment, the first coil is formed by two sub-coils arranged substantially parallel to one another in order to achieve a uniform antenna characteristic.

In a further embodiment, the second coil is formed as a longitudinal coil, resulting in a high signal-to-noise ratio. In a further embodiment, the second coil can be divisible along the longitudinal direction, and can be composed of coil segments. The advantage of a high signal-to-noise ratio in a circularly polarizing local coil can thus be achieved even for examination regions which are difficult to access.

In a further embodiment, the first coil is a coil which is short in the axial direction, and has one coil section aligned obliquely relative to a plane containing the remaining coil surfaces. The coil can thus be adapted to the anatomy of the examination region, and a high filling factor can be achieved even in the case of examinations of anatomical joints. The other coil surfaces can then be centrally aligned relative to the examination region.

In another embodiment, the interior of the second coil can be shaped to accept a human head in the examination region, and for this purpose has a channel-like recess extending in the longitudinal direction. The cross section of the second coil can thus be closely matched to the anatomical features of the head, the recess serving the purpose of accepting the nose area.

In another embodiment, the coil holder in the form of a mount having a keyway permitting displacement of the holder, and thus displacement of the first and second coils, along the direction of the longitudinal axis of the second coil. After the patient has been placed on the patient support, the second coil can thus be shifted (displaced) into the examination position. While this is being accomplished, the first coil is disposed in the second position, leaving the opening of the second coil unobstructed. After the second coil has been satisfactorily placed in the examination position, the first coil is moved from the second position into the first position, so that the first coil also surrounds the examination region.

DESCRIPTION OF THE DRAWINGS

FIG. 12 is a schematic, end elevational view of an antenna arrangement constructed in accordance with the principles of the present invention for use in a longitudinally oriented basic magnetic field.

FIG. 13 is a schematic, perspective view of the antenna arrangement of FIG. 12.

DESCRIPTION OF THE PREFERRED EMBODIMENTS

Figure 1:
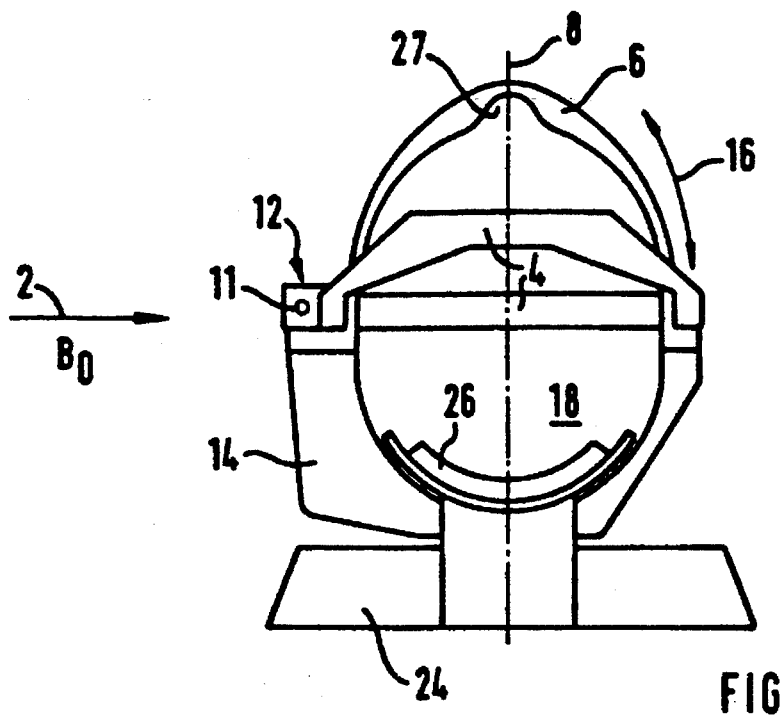
FIG. 1 is a front elevational view of a circularly polarizing antenna constructed in accordance with the principles of the present invention, in an embodiment adapted for examination of a human head.
Figure 2:
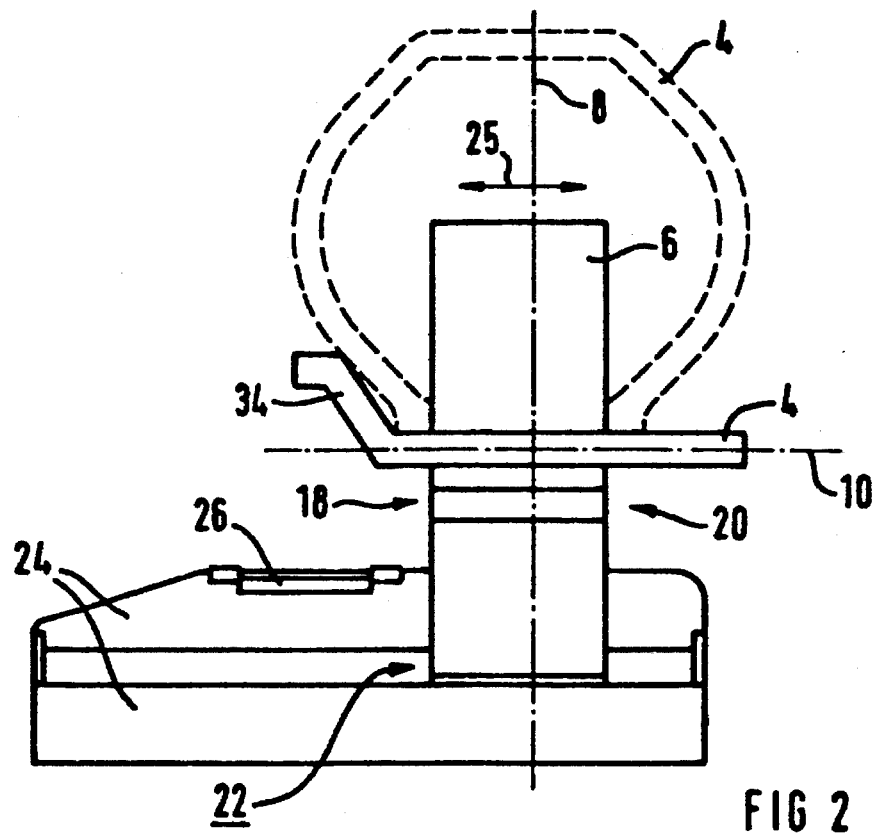
FIG. 2 is a side elevational view of the antenna arrangement of FIG. 1.

One embodiment of a circularly polarizing local antenna arrangement constructed in accordance with the principles of the present invention is shown in a front elevational view in FIG. 1 and in a side elevational view in FIG. 2. This embodiment of the antenna arrangement is adapted for conducting examinations of the human head. The local antenna arrangement is suitable for employment in a magnetic resonance apparatus having a basic magnetic field $B_o$ which proceeds horizontally in a transverse direction, referred to those by skilled in the art as a lateral basic magnetic field $B_0$. The direction of the basic magnetic field $B_o$ is indicated in FIG. 1 by an arrow 2.

The circularly polarizing local antenna arrangement is formed by two sub-antennas, respectively formed by first and second coils 4 and 6. The coil 4 has a coil axis 8 and the coil 6 has a coil axis 10. The coil axes 8 and 10 are oriented perpendicularly relative to each other when the coils 4 and 6 are oriented as shown in FIG. 1, and as shown by the solid lines in FIG. 2. As is known, if the coils 4 and 6 are fed with respective signals which are phase-shifted by 90°, a circularly polarized high-frequency field will be generated in the interior of the two coils 4 and 6 (i.e., the examination region or examination volume). If the arrangement is used as a reception arrangement, the respective reception signals acquired from the coils 4 and 6 are phase-shifted by 90°. The resulting aggregate signal, which is a combination of the respective signals from the coils 4 and 6, will have a high signal-to-noise ratio.

The first coil 4 is short in the axial direction, and the second coil 6 is a longitudinal coil having windings arranged side-by-side. The two coils are each enveloped by a plastic covering, so that the individual turns cannot be seen in FIGS. 1 and 2.

The coils 4 and 6 are both attached to a coil holder 14. The first coil 4 is arranged to be rotatable around a rotational axle 11, for which purpose one end of the first coil 4 is connected at one side of the coil holder 14 by a pivotable joint 12. An arrow 16 illustrates the rotational movement of the first coil 4. The second coil 6 is rigidly connected to the coil holder 14.

The second coil 6 has a front opening 18 and a rear opening 20. When the first coil 4 is in a first position, shown in FIG. 1, the front and rear openings 18 and 20 of the second coil 6 are surrounded (obstructed) by the first coil 4. This is an examination position of the first and second coils 4 and 6, both coils 4 and 6 surrounding the examination region. In order to conduct an examination of an examination subject the first coil 4 is moved to a second position along the direction of the arrow 16, so as to be in the position indicated by the dashed lines in FIG. 2. The examination subject is then moved through the openings of the second coil 6, which are freely accessible while the first coil 4 is in the second position. The first coil 4 is then moved in the opposite direction to return to the first position, as shown in FIG. 1.

The coil holder 14 may be mounted on a base 24, having a keyway 22 which permits the holder 14 to slide along the direction of the longitudinal axis 10 of the second coil 6. This permits the coils 4 and 6 to be longitudinally displaced in the directions indicated by an arrow 25. A head cushion 26 for supporting and fixing the head during the examination is arranged on the base 24. In order to permit the second coil 6 to tightly surround the head, the coil 6 has a channel-like recess 27 in the interior thereof extending in the longitudinal direction, i.e., in the direction of the coil axis 10.

For conducting an examination of the head using the antenna arrangement of FIGS. 1 and 2, the first coil 4 and the second coil 6 are displaced by moving the holder 14 to the right-most position shown in FIG. 2, so that the head of the patient can be seated on the head cushion 26. The first coil 4 is at this time in the second position, i.e., the openings 18 and 20 of the second coil 6 are unobstructed. After the head has been properly positioned, the holder 14 is shifted toward the left, so that the head, and the examination region, are surrounded by the second coil 6 in the final position. The first coil 4 is then pivoted (lowered) so that the first coil 4 surrounds both the second coil 6 and the openings 18 and 20. The examination region is thus surrounded by both coils 4 and 6.

Figure 3:
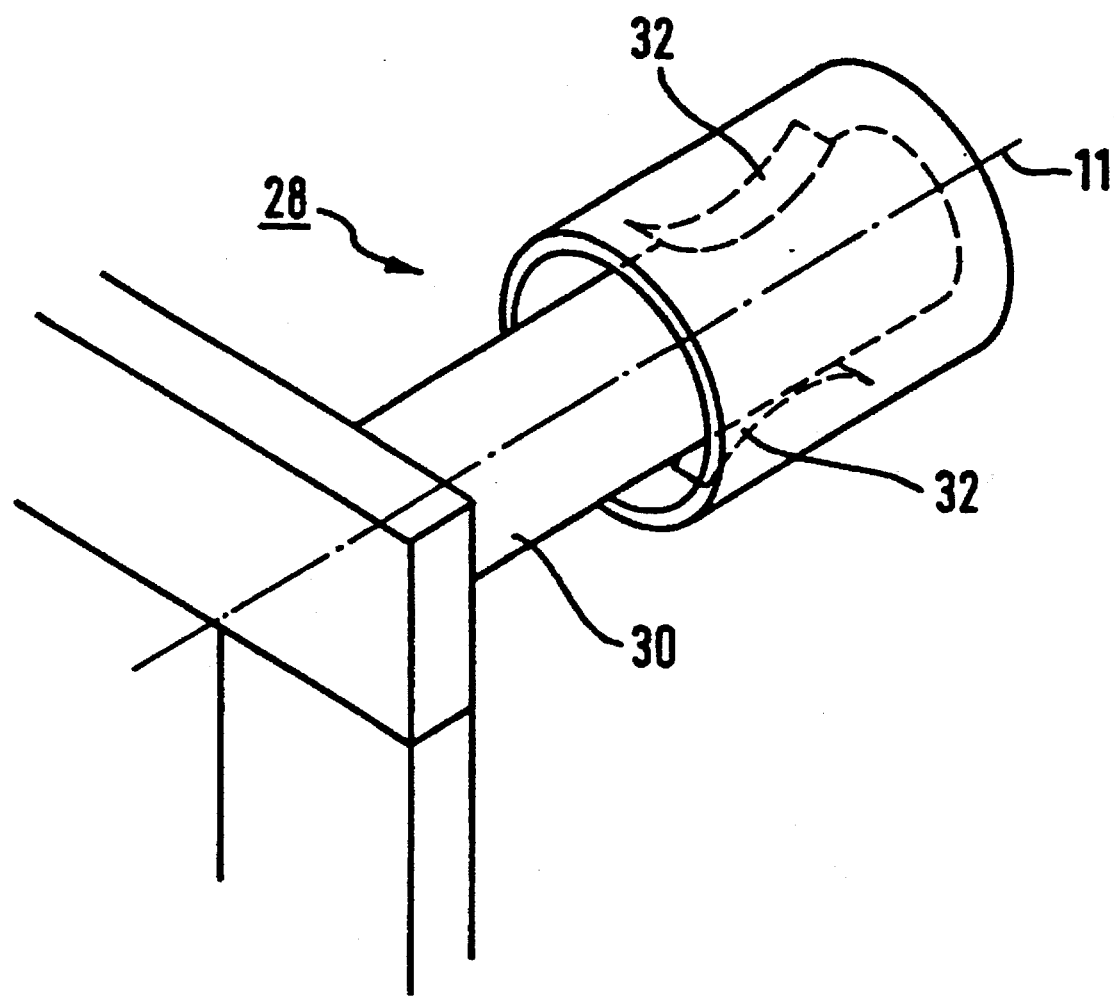
FIG. 3 is a perspective view of an electrical rotary contact employed in the embodiment of FIGS. 1 and 2.

In enlarged detail, FIG. 3 shows a rotary contact 28 which forms a part of the pivotable joint 12. The rotary contact 28 is formed by a stationary, electrically conductive peg 30 which is in contact with electrically conductive spring contacts 32 which are mounted inside a cylinder which is rotatable around the peg 30. The stationary peg 30 is connected to an electrical circuit which includes a matching network, a detuning unit (for reception purposes), and a 90° hybrid circuit. The spring contacts 32 are connected to the coil terminals of the first coil 4.

As can be seen in FIG. 2, the first coil 4 has a coil section 34 which is oriented at an angle relative to the plane of the remaining coil surface. The angled coil section 34 permits the first coil 4 to be aligned centrally relative to the examination region, i.e., relative to the head, despite the anatomical features of the throat and the neck region.

Figure 4:
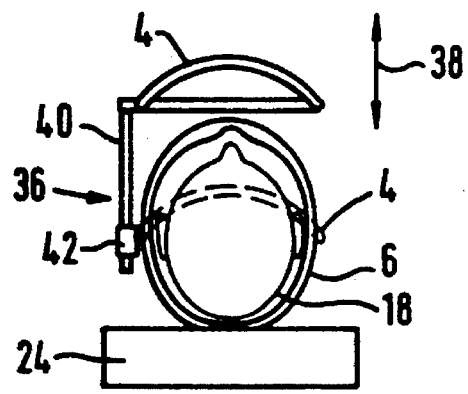
FIG. 4 is a front elevational view of a circularly polarizing antenna constructed in accordance with the principles of the present invention having means for vertically displacing one of the coils.
Figure 5:
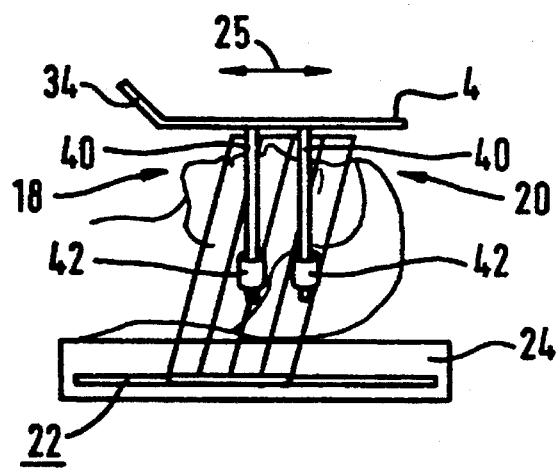
FIG. 5 is a side elevational view of the antenna arragement of FIG. 4.
Figure 6:
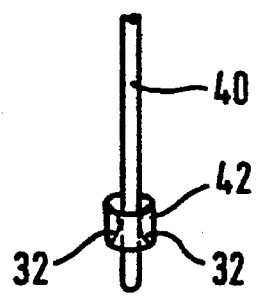
FIG. 6 shows an electrical wiper contact employed in the embodiment of FIGS. 4 and 5.

In the embodiment of the local coil arrangement shown in FIGS. 4 and 5, which is also a head antenna, the first coil 4 is connected to a displacement arrangement 36, which permits the first coil 4 to be moved vertically up and down, as indicated by the double arrow 38. This again permits the front and rear openings 18 and 20 to be left unobstructed for the introduction of the subject into the examination region. The second, unobstructed position of the coil 4 is shown with solid lines, whereas the first position, which obstructs the openings of the second coil 6, is shown with dashed lines in this schematic illustration. The embodiment of FIGS. 4 and 5 is only shown schematically, because the displacement arrangement 36 can be introduced easily into the embodiment of FIGS. 1 and 2, instead of the pivotable joint 12. The displacement arrangement 36 includes a coil holder formed by two glide rods 40 connected to the first coil 4, which are displaceable in a cylindrical guide 42 connected to the base 24, and rigidly disposed relative to the second coil 6. FIG. 6 shows a glide rod 40 in the form of an electrical contact in enlarged detail. To that end, the glide rod 40 is provided with an electrically conductive coating, which is in contact with conductive spring elements 32 contained in the guide 42. The spring elements 32 are connected to the aforementioned electrical circuit, and the glide rods 40 are electrically connected to the coil terminals.

Figure 7:
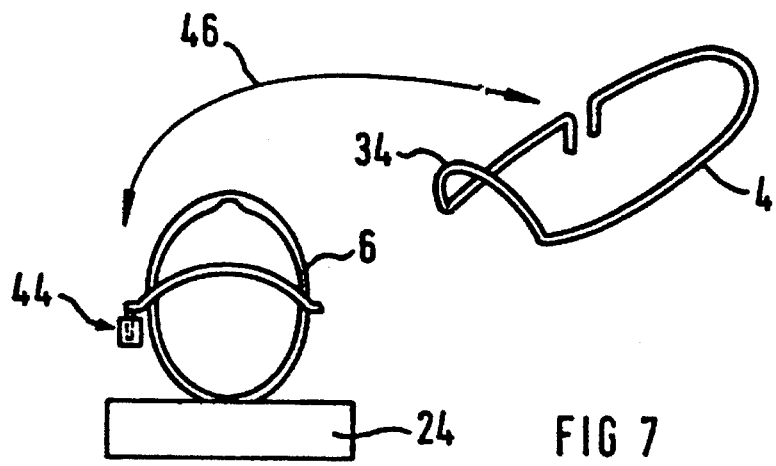
FIG. 7 is a front elevational view of a further embodiment of an antenna arrangement constructed in accordance with the principles of the present invention having a snap-in coil holder.

Another embodiment of a head antenna constructed in accordance with the principles of the present invention is shown in FIG. 7, wherein the first coil 4 is completely separable from the second coil 6 in order to permit introduction of the subject into the examination region with the openings 18 and 20 of the second coil 6 being unobstructed. The embodiment of FIG. 7 employs a snap-in connection 44, which rigidly connected to the second coil 6. The snap-in connection 44 may include electrical connections constructed similarly to those described above, when the first coil 4 is placed therein in the examination (first) position. The connecting and disconnecting of the first coil 4 to and from the second coil 6 are symbolized by the arrow 46.

Figure 8:
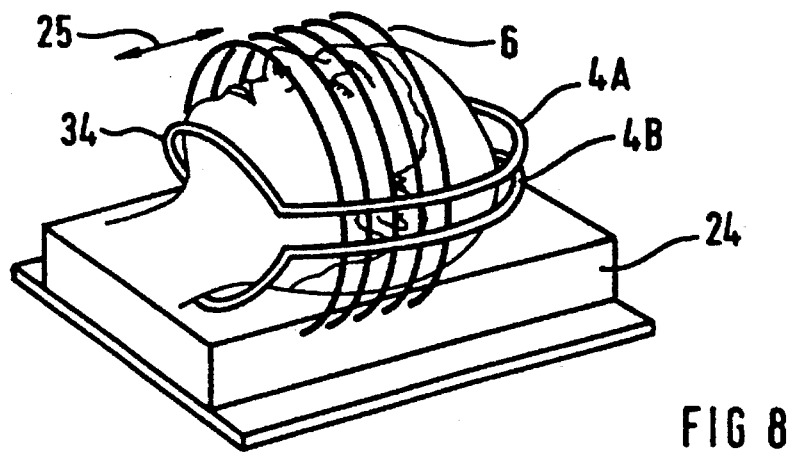
FIG. 8 is a schematic, perspective view of an antenna arrangement constructed in accordance with the principles of the present invention wherein one of antennae is formed by two sub-coils arranged parallel to each other and substantially centrally.

Another embodiment of a circularly polarizing local antenna arrangement in the form of a head antenna is shown in FIG. 8, wherein the antenna characteristic of the first coil 4 is improved in comparison to the above-described exemplary embodiments. To that end, the first coil 4 is divided into two sub-coils 4A and 4B which are disposed parallel to each other. The sub-coils 4A and 4B are electrically connected together in series or parallel. The sub-coil 4A is movably arranged relative to the coil 6. The coil 6 and the sub-coil 4A are displaceable together in the direction of the arrow 25, with the sub-coil 4B being rigidly connected to the base 24. In order to arrange the antenna in the examination position, the head of the subject of the subject is first seated within the coil 4B. The second coil 6 is then shifted to the examination position, with the sub-coil 4A being brought into the examination region thereafter. The fastening of the sub-coil 4A can be accomplished by any of the above embodiments, such as by means of a pivotable joint 12, a displacement arrangement 36 or a snap-in connection 44. The oppositely-angled coil sections 34 of the respective sub-coils 4A and 4B permit the sub-coils 4A and 4B to be arranged substantially centrally relative to the examination region.

Figure 9:
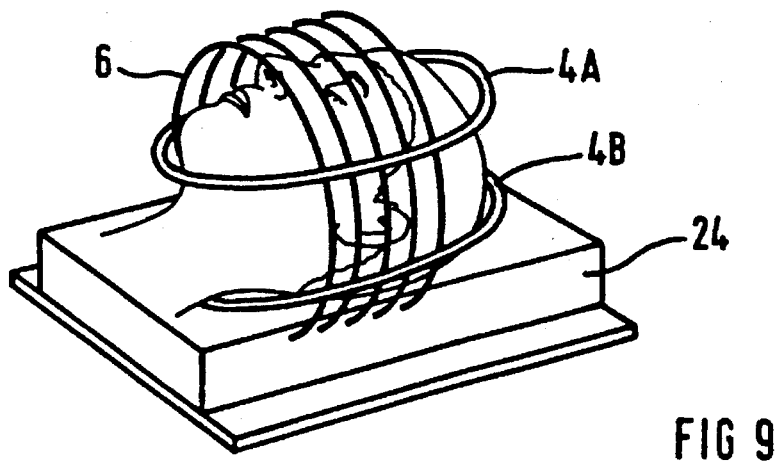
FIG. 9 is a schematic, perspective view of another embodiment of an antenna arrangement constructed in accordance with the principles of the present invention, wherein one of the antennae is formed by two sub-coils arranged parallel to each other and eccentrically.

In the embodiment of FIG. 9, the coil surfaces of each of the sub-coils 4A and 4B are planar, resulting in an eccentric arrangement of the sub-coils 4A and 4B with respect to the examination region. The manipulation of the coil 6 and the sub-coils 4A and 4B for conducting an examination is the same as described with reference to the embodiment of FIG. 8.

Figure 10:
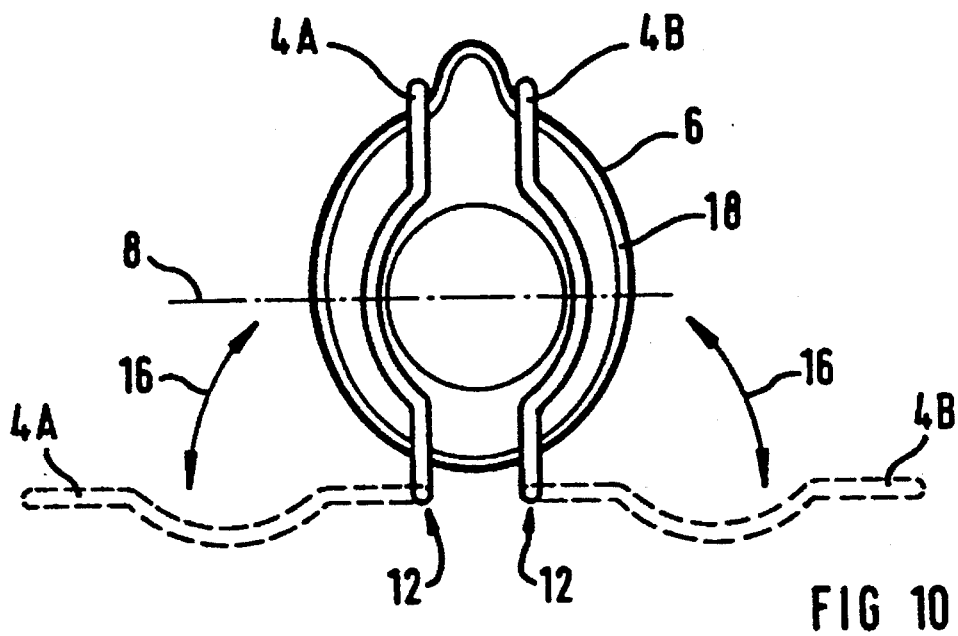
FIG. 10 is a schematic, end elevational view of another embodiment of an antenna arrangement constructed in accordance with the principles of the present invention for use in a vertically oriented basic magnetic field.
Figure 11:
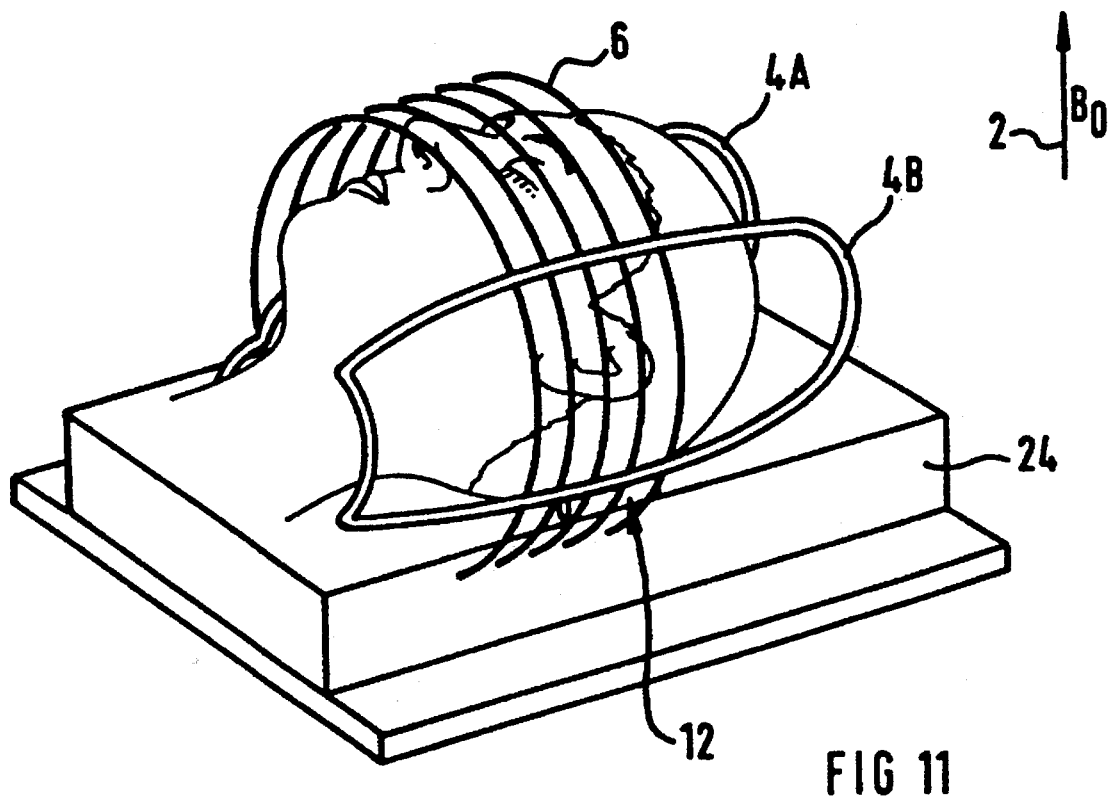
FIG. 11 is a schematic, perspective view of the antenna arrangement of FIG. 10.

FIG. 10 is a schematic illustration of a head coil arrangement for employment in a magnetic resonance apparatus having a vertically oriented basic magnetic field $B_o$. Similar to the embodiment of FIG. 9, the first coil 4 is composed of two sub-coils 4A and 4B, each of which is connected at a bottom thereof to the base (not shown in FIG. 10) by means of pivotable joints 12. The alignment of the basic magnetic field $B_o$ is indicated by the arrow 2 in FIG. 11, which shows the arrangement of FIG. 10 in a perspective view. For introducing the subject into the examination region, the two sub-coils 4A and 4B are moved from the vertical position into the horizontal position shown in FIG. 10 with dashed lines, so that the opening 18 of the second coil 6 is unobstructed for permitting introduction of the patient. The further structural details, not shown in the schematic illustrations of FIGS. 10 and 11, may be the same as shown in the embodiment of FIGS. 1 and 2.

Another embodiment of a head antenna for use in a magnetic resonance apparatus having a basic magnetic field $B_o$ oriented in the longitudinal direction is shown schematically in FIG. 12. In this embodiment, both the first coil 4 and the second coil 6 are divided into sub-coils, the first coil being composed of sub-coils 4A and 4B and the coil 6 being divided into sub-coils 6A and 6B. The sub-coils of each coil are connected in series or parallel. The sub-coils 4A, 4B and 6A are mounted so as to be rotatable using respective pivotable joints 12, so that a region of a patient to be examined can be introduced into the examination region with the coils 4A, 4B and 6B in the opened condition indicated by the dashed lines in FIG. 12. The sub-coil 6B remains rigidly attached, for example, to the base 24.

FIG. 13 schematically shows the antenna arrangement of FIG. 12 in the examination position.

Figure 14:
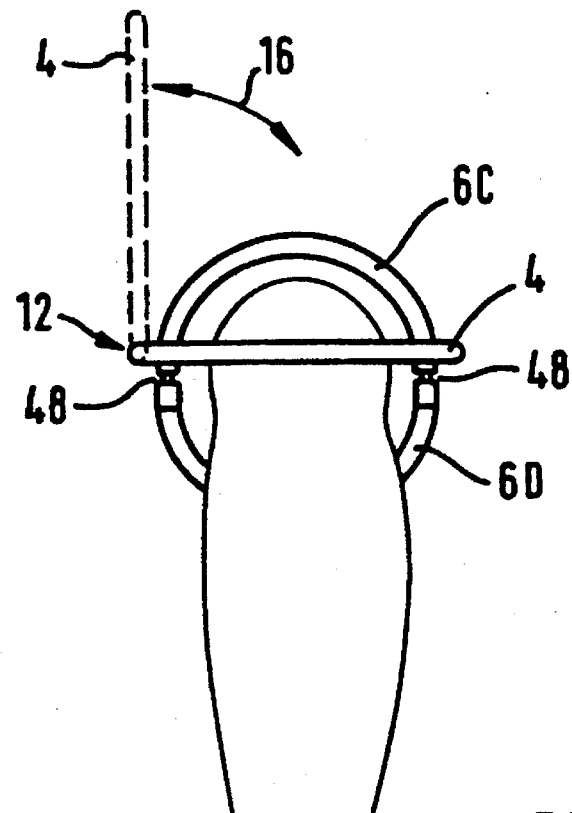
FIG. 14 is a schematic, front elevational view of a local antenna constructed in accordance with the principles of the present invention for conducting examination of the human knee.
Figure 15:
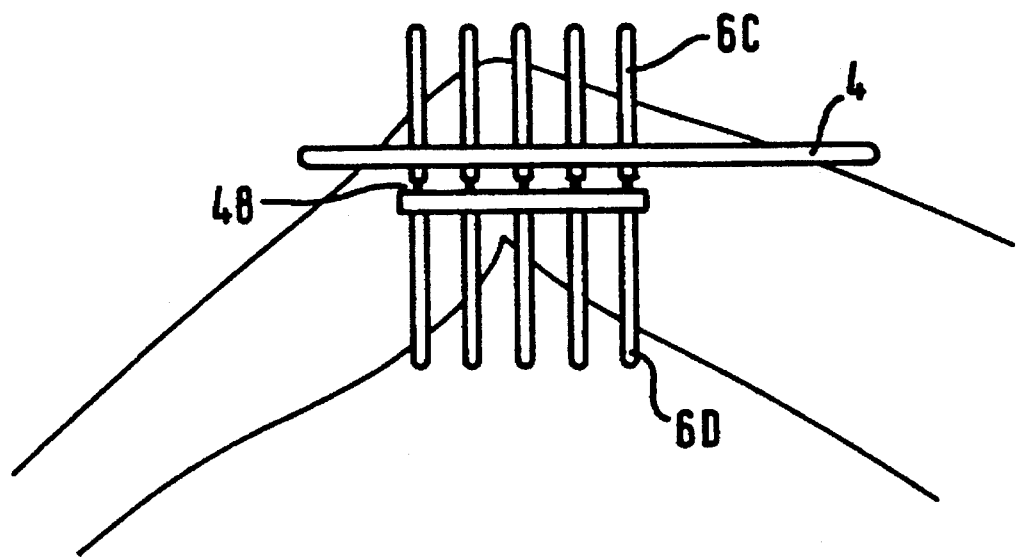
FIG. 15 is a schematic side elevational view of the local antenna arrangement of FIG. 14.

FIGS. 14 and 15 schematically illustrate an application of the circularly polarizing local antenna of the invention for examining a human knee. In this embodiment, the second coil 6 is divisible in longitudinal direction, and is composed of coil segments 6C and 6D. Electrical plug-in contacts 48 electrically connect the coil segments 6C and 6D. The first coil 4 is connected to the second coil 6 by means of a pivotable joint 12. The coil 4 is hinged over the knee for conducting the examination, so that it surrounds both the second coil 6 and the knee joint. The opened position is shown with dashed lines.

Figure 16:
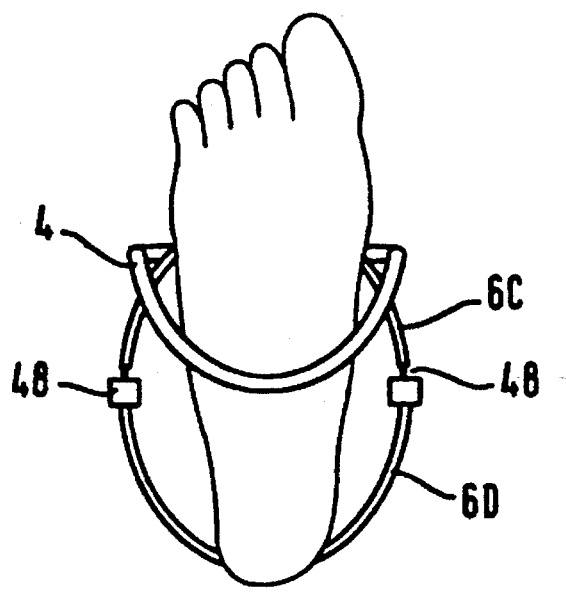
FIG. 16 is a schematic, end elevational view of a local antenna arrangement constructed in accordance with the principles of the present invention for examination of the human ankle.
Figure 17:
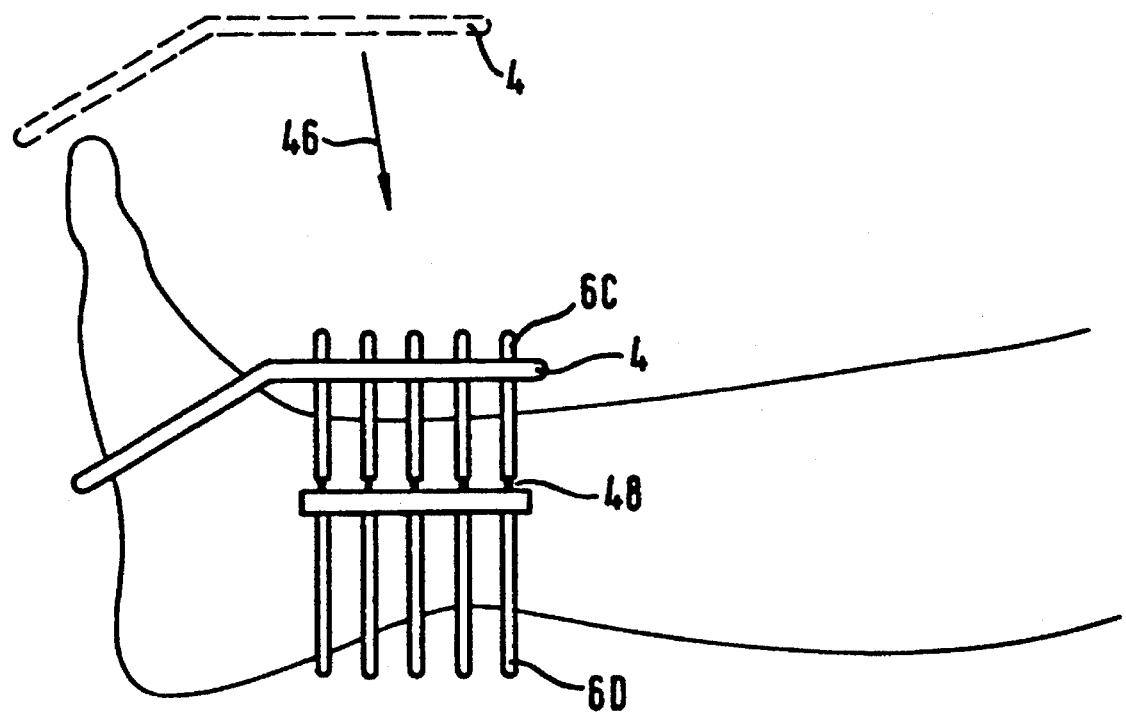
FIG. 17 is a schematic, side elevational view of the local antenna arrangement of FIG. 16.

FIGS. 16 and 17 show an embodiment of a circularly polarizing local antenna arrangement constructed in accordance with the principles of the present invention for conducting an examination of a human ankle. Again, the second coil 6 is divided in the longitudinal direction into coil segments 6C and 6D, so that it can be more easily arranged around the examination region. The first coil 4 is completely separable from the second coil 6, and can be secured to the second coil 6 using the above-described snap in connection 44. The opened position is shown in FIG. 17 in dashed lines, the movability of the first coil 4 being indicated by the arrow 6.

Although modifications and changes may be suggested by those skilled in the art, it is the intention of the inventors to embody within the patent warranted hereon all changes and modifications as reasonably and properly come within the scope of their contribution to the art.

We claim as our invention:

1. A circularly polarizing local antenna arrangement for a magnetic resonance apparatus, comprising:

a first antenna formed by a first coil and having a first coil axis;

a second antenna, separate from said first antenna, formed by a second coil and having a second coil axis, said second coil having an opening surrounding an examination region; and coil holder means, to which said first coil is movably attached so as to be movable between first and second positions and to which said second coil is rigidly attached, for ofrienting said first coil in said first position to surround said examination region with said first and second coil axes disposed substantially perpendicularly to each other and said first coil obstructing said opening of said second coil, and for orienting said first coil in said second position leaving said opening of said second coil unobstructed.

2. A circularly polarizing local antenna arrangement as claimed in claim 1 wherein said coil holder means includes a stationary part and a pivotable joint connecting a lateral side of said first coil to said stationary part, permitting pivoting of said first coil relative to said stationary part.

3. A circularly polarizing local antenna arrangement as claimed in claim 2 wherein said pivotable joint includes rotary electrical contacts for said first coil.

4. A circularly polarizing local antenna arrangement as claimed in claim 1 wherein said coil holder means includes a stationary guide element and at least one rod slidable in said guide element and connected to said first coil, permitting vertical displacement of said first coil.

5. A circularly polarizing local antenna arrangement as claimed in claim 4 wherein said coil holder means comprises two of said rods, each rod having an electrical wiper contact for providing an electrical connection to said first coil.

6. A circularly polarizing local antenna arrangement as claimed in claim 1 wherein said coil holder means comprises a snap-in connection for said first coil, said snap-in connection including electrical plug-in contacts for said first coil.

7. A circularly polarizing local antenna arrangement as claimed in claim 1 wherein said first coil has an axial direction and wherein said first coil is short in said axial direction.

8. A circularly polarizing local antenna arrangement as claimed in claim 1 wherein said first coil comprises two sub-coils disposed substantially parallel to each other.

9. A circularly polarizing local antenna arrangement as claimed in claim 8 wherein each of said sub-coils has an axial direction, and wherein each of said sub-coils is short in said axial direction.

10. A circularly polarizing local antenna arrangement as claimed in claim 1 wherein said second coil has a longitudinal direction, and wherein said second coil is long in said longitudinal direction.

11. A circularly polarizing local antenna arrangement as claimed in claim 1 wherein said second coil has a longitudinal direction, and wherein said second coil is divided in said longitudinal direction into two coil segments.

12. A circularly polarizing local antenna arrangement as claimed in claim 11 wherein said first coil has an axial direction and wherein said first coil is short in said axial direction, and wherein said first coil has a coil section and a coil surface comprised of a remainder of said coil excluding said coil section, said coil section being disposed obliquely relative to a plane containing said coil surface.

13. A circularly polarizing local antenna arrangement as claimed in claim 1 wherein said second coil has an interior having a shape adapted to accept a human head, and includes a channel-like recess extending in a longitudinal direction of said second coil.

14. A circularly polarizing local antenna arrangement as claimed in claim 1 wherein said coil holder means comprises a base and an element to which said first and second coils are attached, said base having a keyway therein along which said element is slidable for displacing said first and second coils in a direction of a longitudinal axis of said second coil.

* * * * *

UNITED STATES PATENT AND TRADEMARK OFFICE
CERTIFICATE OF CORRECTION

PATENT NO. : 5,519,321
DATED : May 21, 1996
INVENTOR(S) : Juergen Hagen and Yutaka Watanabe It is certified that error appears in the above-indentified patent and that said Letters Patent is hereby corrected as shown below:

In column 7, line 1, change "oftening" to "orienting."

Signed and Sealed this

Twenty-seventh Day of August, 1996

Attest:

BRUCE LEHMAN

*Attesting Officer*   Commissioner of Patents and Trademarks